(12) United States Patent  
Moor

(10) Patent No.: US 7,661,301 B2
(45) Date of Patent: Feb. 16, 2010

(54) FLUID ANALYSER SYSTEMS

(75) Inventor: Timothy Nicholas Moor, Corbridge (GB)

(73) Assignee: Elan Vital (UK) Limited, Dalston Carlisle (GB)

( * ) Notice: Subject to any disclaimer, the term of this patent is extended or adjusted under 35 U.S.C. 154(b) by 90 days.

(21) Appl. No.: 10/588,629

(22) PCT Filed: Jan. 27, 2005

(86) PCT No.: PCT/EP2005/000933

§ 371 (c)(1),
(2), (4) Date: Apr. 3, 2007

(87) PCT Pub. No.: WO2005/075962

PCT Pub. Date: Aug. 18, 2005

(65) Prior Publication Data

US 2007/0256477 A1    Nov. 8, 2007

(30) Foreign Application Priority Data

Feb. 5, 2004    (GB)    ................................. 0402532.6

(51) Int. Cl.
*G01F 17/00* (2006.01)
(52) U.S. Cl. ........................................................ 73/149
(58) Field of Classification Search ................ 73/23.35, 73/23.2, 23.37, 149, 61.48, 61.52, 53.01
See application file for complete search history.

(56) References Cited

U.S. PATENT DOCUMENTS

| | | | | | |
|---|---|---|---|---|---|
| 3,854,050 | A | * | 12/1974 | Peterson et al. | ............. 250/429 |
| 4,243,322 | A | * | 1/1981 | Ingalz | ......................... 356/244 |
| 4,548,907 | A | * | 10/1985 | Seitz et al. | ................... 436/163 |
| 4,851,683 | A | | 7/1989 | Yang et al. | ................... 250/339 |
| 5,061,076 | A | * | 10/1991 | Hurley | ......................... 356/417 |
| 5,064,283 | A | * | 11/1991 | Tober | ........................... 356/73 |
| 5,840,572 | A | * | 11/1998 | Copeland et al. | ......... 435/286.7 |
| 6,300,638 | B1 | * | 10/2001 | Groger et al. | ............. 250/458.1 |
| 2002/0135282 | A1 | | 9/2002 | Hudak | ................... 313/231.31 |

FOREIGN PATENT DOCUMENTS

| | | |
|---|---|---|
| JP | 2003 344290 | 12/2003 |
| WO | 03/043738 | 5/2003 |
| WO | WO 03/044503 | 5/2003 |

* cited by examiner

*Primary Examiner*—Hezron Williams
*Assistant Examiner*—Gunnar J Gissel
(74) *Attorney, Agent, or Firm*—Ohlandt, Greeley, Ruggiero & Perle, L.L.P.

(57) ABSTRACT

The radiation emitted by the various components in a sample of a fluid wherein the radiation emitted by activated molecules within the sample of the fluid is used to determine the nature of and quantities of materials present in the fluid and a fluid analyser system comprising a receptacle(s) and an analysis apparatus containing a consistent light condition compartment containing temperature detection device(s) into which the receptacle containing the fluid sample may be placed and means are provided for activating the molecules within the sample so that the radiation emitted by the sample may be detected and amplified.

24 Claims, 9 Drawing Sheets

Exploded view

Cross section of receptacle cross section

Flow of fluid

Flow of fluid

Figure 5
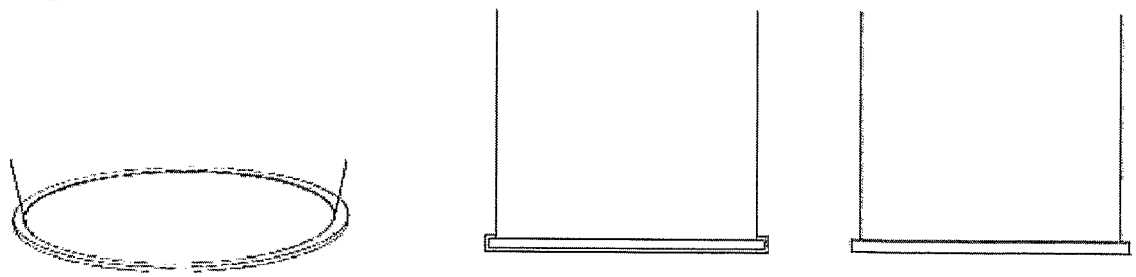
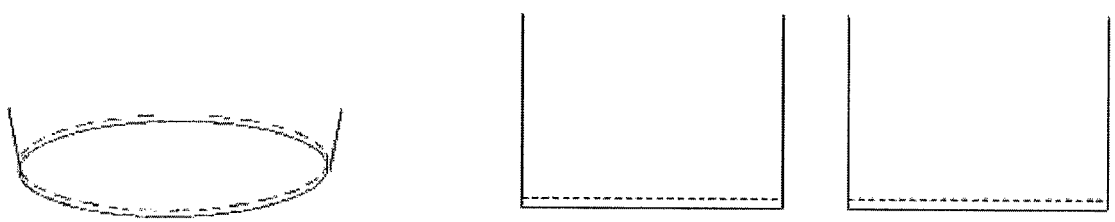
Figure 6
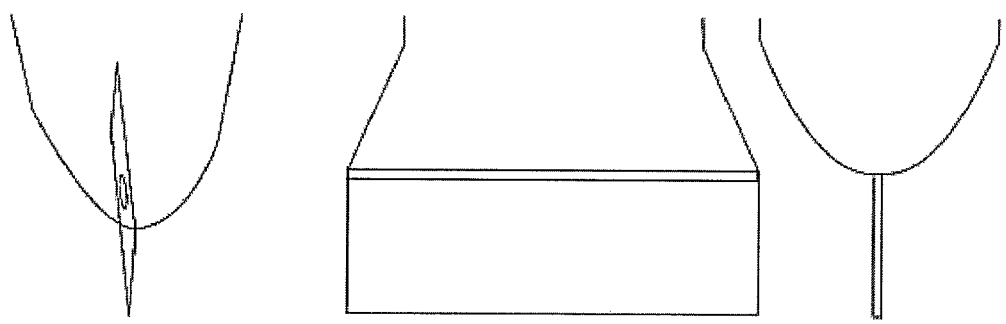
Figure 7
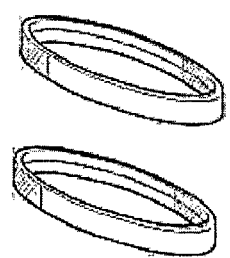

Ready to use
before collection

A

Inflated receptacle
after collection

B

Figure 10. Schematic flow diagram of the performance of the system of the present invention Figure12. Fluid Analyser System's Information Flow

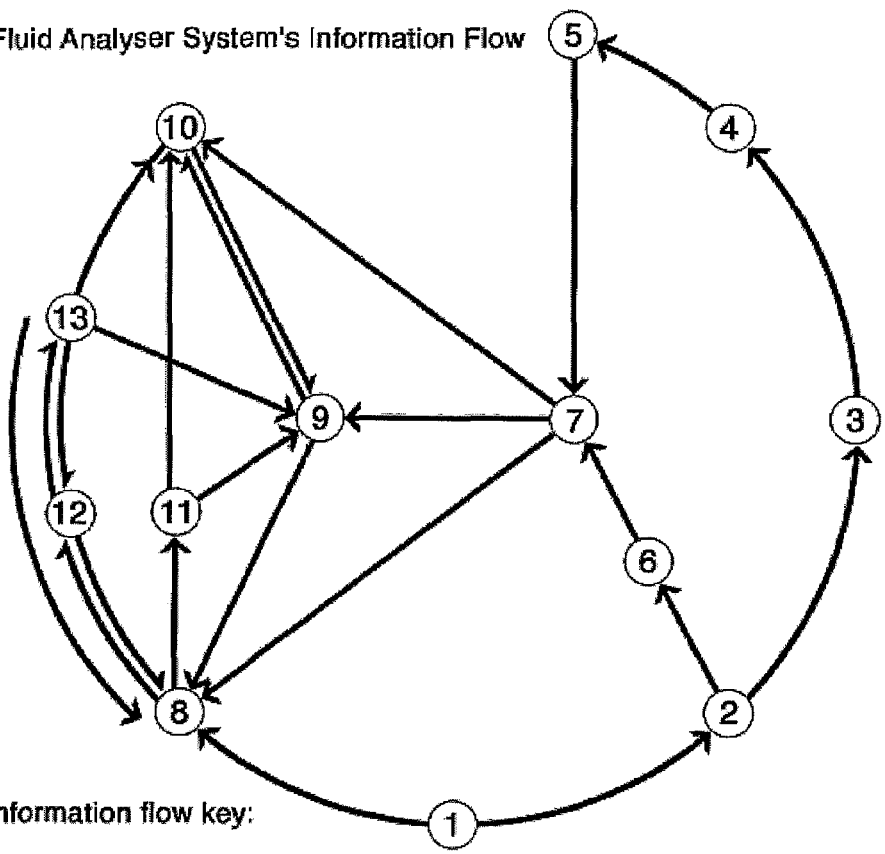

Figure 12 Information flow key:

① Remote/ Physical Start-up Digital Re-calibration

② Start selected test

③ From sensors receive raw data

④ Calibrate and/or Average/ Magnify data

⑤ Search fluid database

⑥ Test Procedural, Tagging and/or Conditions data;
Individual, Environmental and/or engine reference data ⑦ Advisory status report with reference information ⑧ Store/ Search ⑨ Comparitive Analysis ⑩ Print ⑪ Internal data ⑫ Remote transfer/ receive ⑬ External data/ databank

FLUID ANALYSER SYSTEMS

CROSS REFERENCE TO RELATED PATENT APPLICATIONS

This instant patent application is a National Stage Filing of, and claims priority to, International Patent Application No.: PCT/EP2005/000933 filed on Jan. 27, 2005, and claims priority to British Patent Application No.: 0402532.6 GB filed on Feb. 5, 2004, which are herein incorporated by reference in their entirety.

BACKGROUND

1. Field of the Invention

The present invention relates to fluid analysers and in particular it relates to improved forms of fluid analysers capable of determining the composition of the fluid, particularly the chemical composition. In particular the invention relates to analysers which are simple to operate and are both qualitative and quantitative in identification of the components within individual and/or a multitude of fluids. The invention enables analysis to a high degree of accuracy without having to change or put additional fluid analyser sensors into the system.

2. Discussion of the Background Art

Most analysers rely upon sensors gathering information from within frictional flow rates of fluids. However, the analyser of the present invention works by collecting the fluid sample via a non-invasive methodology and thus avoids contamination of the fluid to be analysed. In a preferred embodiment the invention relates to a fluid analyser that is portable and may be used to analyse the samples taken at a remote location and to interact with other fluid analyser systems usually of the same manufacture. This permits use of the analyser in a wide variety of environments and settings.

For the purpose of this document, Fluid means:
i) Consisting of any particles that move freely among themselves;
ii) "particle" means, a minute portion of matter;
iii) "matter" means, any of numerous subatomic and/or atomic constituents of the physical world that interact with each other;
iv) "constituents" means, anything that occupies a space.

Portable fluid analysers are known and the breathalyser used to detect alcohol in a motorist's breath is an example of a portable fluid analyser. Portable, or mobile, analysers are also used for environmental purposes such as the determination of air purity around petrochemical complexes, gas fires and boilers. Portable or mobile analysers are also used in mining and in other hazardous activities to detect the presence of dangerous fluids.

Existing portable fluid analysers consist of a sampler and an analyser. They do however, suffer from certain disadvantages. Firstly the fluid sampler and the analyser make up a unitary apparatus with operators manning and being required to understand the complexities of the analyser. Furthermore, the results of the analysis cannot usually be compared on the spot with previous data because the previous data is generally stored in a remote location. An additional disadvantage is that typically portable analysers can usually detect no more than 4 gases in a fluid sample at any one time and specialty analysers can usually detect no more than 6 at any one time. The traditional analysers are further limited in that when working on gaseous mixtures they cannot detect a concentration above and/or below a saturation limit which depends upon the nature of the gas.

Existing fluid analysers tend to detect fluids in a flow of fluid in a stream as it passes a detection probe or probes. This technique suffers from the drawback that the probe must be cleaned after each analysis before any subsequent use and it is difficult to get the probe sufficiently clean to prevent contamination for the next test. Also it is sometimes necessary to recalibrate the probes between each analysis. In many existing fluid analysers each fluid is detected by means of an electro chemical sensor and the user needs to replace the sensor according to the fluid to be detected. It is then necessary to recalibrate the sensor to detect another fluid.

If the flow rate in one analyser is greater than that of another and the sensors are the same. The device with the greater frictional flow rate will normally provide a more accurate reading. However to obtain an even greater accuracy and a wider range of fluid analysis, a radioactive scan in a predetermined environment has been proposed to provide greater accuracy and quantity analysis report.

Chemiluminescence is sometimes used for gas analysis and involves the capturing and interpretation of emitted light during a chemical reaction. Absorption and desorption rates of molecules on surfaces of fluids and their transfer rates from a surface of a fluid are dependent upon temperature. This action is termed surface diffusion and where there is an equilibrium both absorption and desorption occur creating corresponding fluxes of equal magnitude. This type of analyser suffers from the disadvantage that it relies on thermal or chemical reactions induced or otherwise to analyse the intensity values of fluids and thus determine the amounts of fluids that are present.

Gas Chromatography is also used for fluid analysis. This technique separates a mixture of fluids by passing it in solution or suspension through a medium in which the components move at different rates to enable identification of the different components present in the mixture. The fluid analyser system of the present invention however, has no need to pass the sample in the container through a mixture or suspend it in a liquid in order to assess the identity of the contents or their volume within the sample.

It has also been proposed that fluids may be analysed from the reconstructed gas/fluid emissions formed and identified by the addition of chemicals in a calculated manner. The surface relaxation of fluids has the causal effect of emitting a variable light. The variable light from the chemical reaction helps create the environment where electrons invade the x, y and z axis through a process of spilling. Friedel oscillations are created near the surface of fluids which may or may not screen the ions. Where the ions are allowed to withdraw back into the surface of a material the energy received from the material will be reduced or changed. The changes can be used to indicate the nature of the components of the fluid; this process however suffers from the disadvantage that it relies on a chemical reaction.

The refractive index is used to differentiate the light reflected back from different substances thereby providing an identity; however, the light cannot be clearly identified much beyond 6 decimal places which have the disadvantage of categorising different substances under the same refractive index number.

Mass Spectrometry can also be used. The objective of the Mass spectrometry is to separate each mass from the next integer mass and this can be achieved in several ways the first of which is via Unit resolution mass 50 distinguishable from mass 51, for example. The magnetic sector using the Gaussian Triangle peak method of differentiation. The Fourier Transform Ion Cyclotron Resonance (FTICR) system utilises twin peaks with a Lorentzian shape and 10% valley resolution. The Time of Flight (TOF) mass spectrometer is resolved to a 50% peak-height definition incorporating the Gaussian triangle shape. The two peaks are resolved to a 50% valley.

Mass Spectrometry is concerned with the separation of matter according to atomic and molecular mass. It is most often used in the analysis of organic compounds of molecular mass up to as high as 200,000 Daltons, (Atomic Mass Unit) and until recent years was largely restricted to relatively volatile compounds. Continuous development and improvement of instrumentation and techniques have made mass spectrometry the most versatile, sensitive and widely used analytical method available today. However, the fluid analyser system of the present invention is capable of a definition of a fluid particle beyond that of a mass spectrometer. Furthermore, the analysis of the present invention utilises captured sample/s where integrity of the sample is maintained. Mass Spectrometry also suffers from the difficulty that integrity is problematic.

In Mass Spectrometry radiation sources, such as lasers, are used, the wavelength of current lasers occurs in approximately the visible wavelengths. Conversion of visible wavelengths into shorter wavelength radiation has many practical applications beyond the intrinsic theoretical interest in production mechanisms, as absorption sources, x-ray heating sources, x-ray lasers. Radiation is amplified through laser energy aimed at the sample. The fluid analyser of the present invention does not require additional energy radiation in order to amplify the signal radiative source of the fluid in the sample container to facilitate the identity of the fluid.

U.S. Pat. No. 6,271,522 suggests that spectrometry may be used for gas detection. Similarly U.S. Pat. No. 5,319,199 uses infrared and ultra violet radiation to detect the gases present in vehicle emissions. U.S. Pat. No. 4,746,218 is concerned with spectral absorption to detect and analyse gases. None of those devices enable the simultaneous detection and analysis of a multitude of gases and none of them can detect gases at a low enough concentration to be useful in, for example, comprehensive medical diagnosis.

Our published PCT Application WO 03/044503 relates to a fluid analyser system, in particular a portable fluid analyser system which overcomes the various disadvantages previously described. The analyser of PCT publication WO 03/044503 does not require probes in the fluid to be analysed and operates on a self contained static fluid sample which thus minimises or avoids contamination of the sample. The analyser of PCT Publication WO 03/044503 has the additional benefit that the sample once taken remains sealed to prevent contamination and that the sample can be stirred.

SUMMARY OF THE INVENTION

The present invention provides an improvement over the analyser described in PCT publication WO 03/044503 enabling even greater accuracy in detection and quantification of components in fluid sample. The fluid analysers of the present invention can be used to develop personal breath profiles which can be stored somewhat like a fingerprint and the stored profile can be checked against a new sample taken at a later date or during health checks.

The present invention further provides a receptacle for a fluid sample which can be used in the fluid analysis techniques of the present invention.

Accordingly, we have now found that if the molecules within the fluid sample are excited during the scan according to the process of PCT Application WO 03/044503 the signatures of the individual molecules present in the sample can be defined more clearly.

Accordingly, the present invention provides a process for the detection of the radiation emitted by the various components in a sample of a fluid wherein the radiation emitted by activated molecules within the sample of the fluid is used to determine the nature of and quantities of materials present in the fluid.

Accordingly in one embodiment the present invention provides a fluid analyser system comprising a receptacle(s) for the collection of a fluid sample and an analysis apparatus containing a consistent light condition compartment containing temperature detection device(s) into which the receptacle containing the fluid sample may be placed, means within the consistent light condition compartment for activating the molecules within the sample and means for detecting the radiation emitted by the sample, together with means for magnification of the detected signal.

In addition the present invention further provides means for translating the magnified signal into the nature and quantity of the fluids present in the sample said means being referenced according to:

a) the known volume of the inflated receptacle
b) the light condition of the fluid sample
c) the temperature of the fluid sample
d) the duration of the radiation scan and/or
e) the distance of the radiation scan.

The present invention further provides a fluid analyser system comprising:

i) A receptacle for a fluid sample.
ii) A consistent light condition environment in which the receptacle can be placed.
iii) A timing device for measuring duration of the scan of the radiation emitted by the fluid sample in the receptacle.
iv) A temperature sensor for determining the temperature of the sample.
v) Means for activating the molecules within the sample.
vi) Detector(s) for receiving data from the radiation emitted by the sample located at a predetermined distance from the sample.
vii) Means for translating and magnifying the signal from the detector(s) enabling identification of the intensities and the peak intensity values' wavelengths.

Optionally the system may also include a light meter for determining the consistent light condition environment.

BRIEF DESCRIPTION OF THE DRAWINGS

FIG. 2a shows a sample bag with two pinholes in the side walls;

FIG. 2b shows a cross-section through line X-X of FIG. 2a;

FIG. 5 is a view of the bottom of a receptacle comprising a solid or flexible but not elastic base with no valve according to another embodiment;

FIG. 6 is a view of the bottom of a receptacle comprising a sample bag sealed to itself according to another embodiment;

FIG. 7 is a tamper-proof clip and/or weld used to seal the sample bag to the valve holder;

FIG. 12 is a flow chart of an information flow during an analysis performed according to the present disclosure.

DETAILED DESCRIPTION OF THE PREFERRED EMBODIMENT

Figure 1:
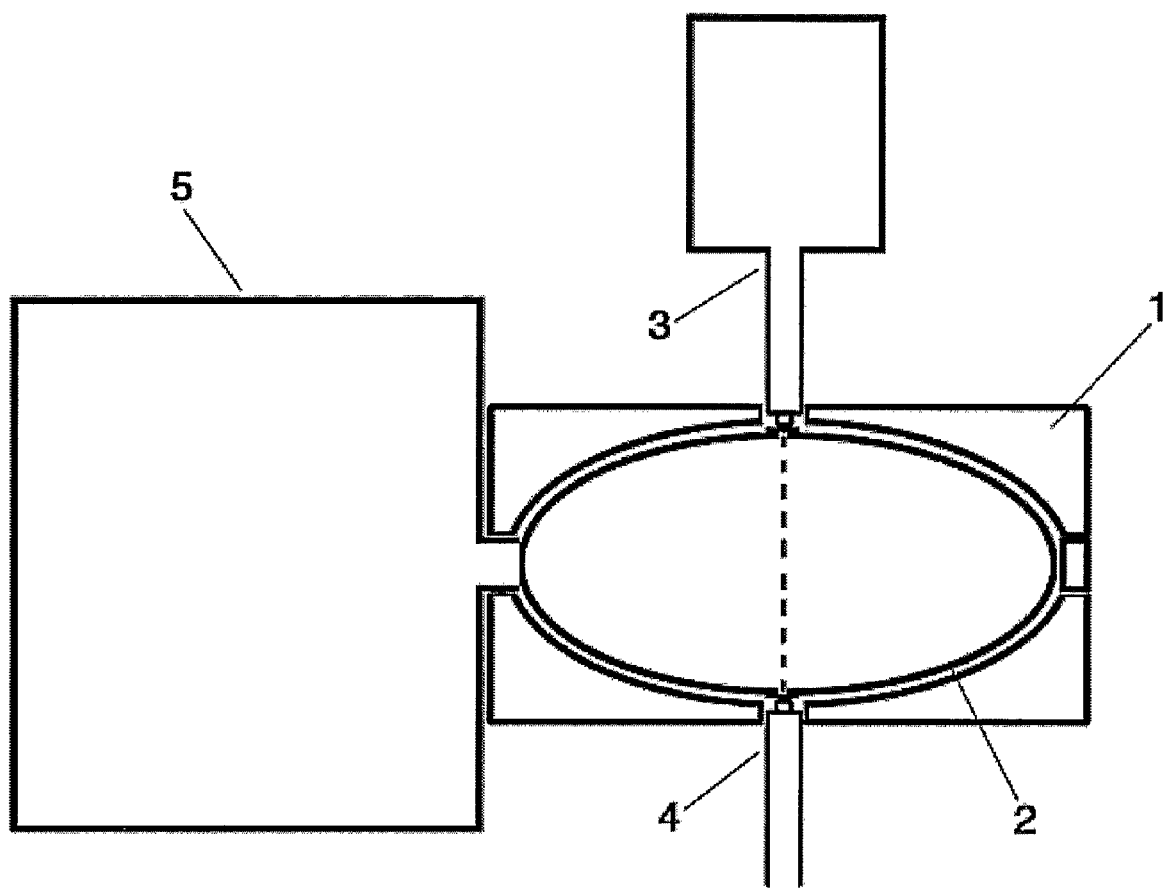
FIG. 1 is a cross-section view of a sample analysis section of an apparatus used in the present disclosure.

The intensities and intensity values of the peaks detected may then be used/calculated and/or correlated with either known/unknown peak intensities and/or peak intensities values (nm wavelength values) to indicate the nature of the fluids present in the sample and to determine the concentrations of the fluids in the sample.

The device for activation of the molecules may be any suitable activation device. However, we prefer that the device provide radio frequency discharge (using for example a Tesla coil). Alternatively the excitation process may be accomplished using various light sources. If a light source is used we prefer to use a lamp rather than a laser since use of a laser would involve mirrors and complex additional absorption issues. The choice of activation energy depends to some extent on the nature of the container used to hold the sample. For example if UV light is used and the container is made of FEP (polytetrafluoroethylene) we have found that excitation below 200 nm is ineffective because transmission through FEP is negligible at this level. Examples of suitable activation sources include white light sources, UV, halogen quartz, sodium and mercury lamps. Radio frequency excitation is however preferred. Although the fluid analysis system shows the signatures of the light source excellently we have found that the radio frequency discharge device provides the clearest signature of the molecular content of the sample and provides an accurate quantitative and qualitative analysis of the components of the fluid.

We prefer that the excitation device is located within the constant light condition compartment so that excitation takes place in a plane perpendicular to the Radiation Absorption Device(s) so that the activation energy is transverse to the absorption device. It is important that the consistent light environment chamber remains consistent and is preferably dark. It is also preferred that the excitation device is operational/active through the duration of the radiation absorption device's scan.

The radio frequency discharge device has the added advantage that it covers all the required wavelengths, whereas a light source covers narrower but known wavelength range. In either embodiment the excitation device has a known signature, which can be subtracted from the actual sample reading and the actual dark level reading. This therefore enables the detection and determination of the signatures of the molecules inside the fluid receptacle.

Use of a radio frequency discharge device requires the provision of a metallic object positioned to direct the radio frequency or to define a break or gap in the discharge circuit. This creates a form of consistent 'lightening' between the discharge device circuit wires (gap) and/or the metallic object. By way of example the 'lightening' is similar to that of a handheld gas lighter for domestic gas cookers. The difference is that in the present invention the discharge is consistent for the required duration of the radiation absorption scan over a pre-determined distance.

The detector(s) used in the present invention is preferably a Radiation Absorbance Device(s) (RAD) which receives the radiation levels according to the nano metre wave energy received from fluid(s) within the sample of fluid as recorded over a predetermined time span via a divided amalgam-coated glass or other appropriate material surface. The surface records the radiation levels received at the specific nano meter wave divided cells (Charge Coupled Device, CCD). These cells are convenient indicators used for the purpose of identification of the sample fluid and its intensity volume.

This system may operate via a specially designed, fully coordinated, computer driven software system to provide an advisory status report of the content of the fluid and the conditions under which the test was performed.

The analyser system of the present invention preferably also includes a means for the measurement of the humidity and dew point of the sample and also means for determining the atmospheric pressure. These measurements can be stored to enable these factors to be taken into account if and when the profile obtained by the analysis is compared with another sample or for reference purposes. This may be the case when the analyser is used for fluid/emission analysis for health and environmental purposes. In a further preferred embodiment the system is provided with a GPS so that the date, time and location (altitude, longitude and latitude) of the position where the sample was taken can be recorded.

The system preferably also includes a means for the measurement of gravity, sound and vibration, velocity and direction.

The analysers of the present invention can detect the presence of a multitude of fluids in a sample and they can also detect the presence of the amounts of fluids present as low as parts per billion and lower.

The fluid analyser of the present invention has the benefit that it may be used at anytime by trained operators in most environments and conditions. Furthermore, the analyser system is versatile. For example, the sample may be taken at one location and the scanning and analysis system may be used in the same or another location. The detection signal, either via a remote control or operator, may then be transferred to another location for magnification, analysis and/or storage or kept in the same location for magnification, analysis and/or storage. Data may also be received in the same manner and this data and any other stored data may be used for comparative purposes being checked against any previous or current internal and/or external test results. If the data analysis system is at a different location from the sample taken, it is preferable to install relevant reference data into the fluid analyser system including the time, conditions and location of where the sample was taken. Maintaining the integrity of the reference data.

The techniques of the present invention may be used in an industrial environment for the detection of gases in particular pollutants and toxic gases in for example mines, chemical plant, oil rigs, oil wells and the like. The techniques may also be used for determining the contents of air and their concentrations at any location such as the workplace, home or car. It may also be used in the evaluation of engine combustion, the emissions generated and their interaction with the environment. It is particularly useful in the detection of the presence of particulates in fluids taken. This is useful in the monitoring of engine performance, which is becoming increasingly important as environmental legislation becomes more severe. This is particularly relevant to diesel engine performance. The techniques may also be used for, but not limited to, environmental studies where atmospheric changes are significant such as in weather forecasting and forecasting, volcanic eruption and earthquakes. Additionally, the analysers can be used to detect different gases or combinations of gases that plant life can produce prior to earthquakes.

A particular use of the techniques of the present invention is in the detection of the content of human and animal breath. The techniques therefore may be used in the production of data for the monitoring of human health. In addition, the ability to take and scan samples in one location, such as in the home, in an ambulance or at an accident site and transmit the results to, for example, a doctor's surgery or a hospital for analysis and the production of results can enable more rapid diagnosis and treatment.

In whatever environment the present invention is used in order to determine the identity and volume, a sample of the fluid to be analysed is first collected in a receptacle(s). In order to get a sharp image of the radiation emitted by the sample the walls of the receptacle should have a high optical clarity. The side walls of the receptacle should be flexible but not elastic. The receptacle is preferably provided with a one-way valve to enable it to be filled through the one-way valve. The valve will prevent escape of the introduced fluid and ensures that the receptacle is automatically closed when it is full. The receptacle should be such that there is minimum contamination. The size and the shape of the receptacle is not important and will depend upon the environment in which the analyser is used.

The materials used to make the receptacle should have minimal absorption and dispersion rates and withstand potentially very high temperatures. The walls of the receptacle are preferably thin to improve the optical clarity and the accuracy of the fluid sample temperature.

The degree of optical clarity required will depend upon the use to which the receptacle is to be put. However, when used for fluid analysis high clarity is required as indicated by the transmission of a high percentage of ultra violet and visible light. A solar transmission, as determined by ASTM E-424, greater than 90% preferably greater than 95% is preferred. For this reason fluorocarbon films such as FEP available from Du Pont is a preferred material for the production of receptacles especially those to be used in gas analysis. Use of FEP and like materials has the added benefit that it cannot be compressed.

The walls of the vessel are preferably flexible and inelastic. Flexibility means that the material at its thickness of use is able to completely recover its original shape and form from compression, concertina, flat pack, fanfold, stack, bend or twist. This comprehensive flexibility simultaneously maintaining the integrity of their contents within a high optical clarity material. Inelasticity ensures that the receptacle cannot be expanded beyond its desired volume.

In one embodiment rigidity may be imparted to part of the vessel structure through the incorporation of a rigid moulded part such as the top and/or the base of the receptacle. The integrity of the contents is still maintained as aforementioned, however the optical clarity is sacrificed at top and bottom of the receptacle in favour of rigidity and strength.

Receptacles that may be used are desired in PCT Publication WO 13/044503. However, a preferred form of a receptacle of the present invention for use in the collection of samples is now described.

The receptacle is conveniently made by mass produced methods and we have found that fluorocarbons such as FEP (polytetrafluoroethylene), preferably virgin FEP, supplied by Du Pont, MFA supplied by Ausimont and PFA are particularly useful materials from which the sample bag can be made. The discharge used to activate the molecules in the sample will follow the path of least resistance and it is important to control the discharge through the sample bag and to keep the discharge path constant. We have found that this may be achieved in a preferred embodiment of the invention if at the point in the consistent light environment chamber where the receptacle is positioned against the RAD(s) the shape of the receptacle is oval with the widest point next to the RAD(s). In this preferred embodiment a pinhole is provided through the sample bag's upper and lower wall with metallic contacts positioned to cover the pinholes creating a seal. The pinholes are preferably the same diameter as that of the discharge and they guide the discharge through to the contents of the container and thus ensure consistent analysis. We have found aluminium adhesive tape is a particularly effective sealing tape especially due to its excellent conductive nature, flexibility, strength and seal. We prefer to use seals in the shape of cylindrical tabs. However, any appropriate metallic contact which provides a seal may be used and it may be of any desired fitting, thickness and shape.

The sample bag is preferably extruded, seamless and is preferably provided with an opening into which the valve holders and valves can be clipped and/or sealed. We also prefer that the side walls or bag of the receptacle have a thickness of from 25 µm to 150 µm, 40 µm to 125 µm, more preferably 45 µm to 105 µm most preferably of approximately 100 µm.

At the time of collection of the sample of the fluid to be analysed it is preferable that the temperature of the sample should be measured and recorded together with other significant information such as the humidity, atmospheric pressure and location.

At the time when the fluid sample in the receptacle is to be analysed by the fluid analyser, it is also preferable to determine the temperature of the fluid sample. A mechanism is preferably provided for a temperature probe to be inserted through a wall of the consistent light environment chamber to touch the skin of the sample bag contained within the consistent light environment. The probe without penetrating the skin makes contact with the sample bag. Due to the flexible nature of the sample bag, the wall of the bag can surround the temperature probe encasing the tip and the fluid analyser system can then start taking measurements. The mechanism driving the temperature probe is controlled by variable resistance ensuring for each time the probe is positioned it will be encased by the bag but penetration is prevented. Measurements of the ambient temperature of the consistent light environment chamber can also be taken and recorded. The light environment chamber is preferably made of a single material to reduce radiation contamination. It should be opaque and polypropylene is a suitable material. It is preferred that no resins or adhesives be used in the manufacture of the light environment chamber.

The duration of the scan is pre-determined. The measurement of duration is the receiving device(s)'s allowable exposure time to the radiation emitted by the activated fluid sample. From start to finish the time increment can vary according to the user's requirements typically ranging from but not limited to milliseconds up to 7 seconds and beyond. As previously mentioned it is preferred to use Charge Coupled Device (CCD) detectors to register the radiation emitted by the sample.

Further arrangements may also be made for the determination of the humidity and thereby the dew point. It is however important that the sensors do not penetrate the skin of the container so that there is no physical interference with the fluid sample.

In the preferred operation of the present invention once inflated with the sample of the fluid to be analysed the receptacle is placed into the consistent light condition, preferably dark environment compartment next to a detector which is preferably a Radiation Absorbance Device(s) (RAD). The compartment should then be closed so that normal light will not interfere with the analysis of the fluids and the light reading in the compartment can then be measured and recorded. The activation device is then started up providing a discharge through the sample. The process variables such as temperature, pressure and humidity are then measured and recorded. The Radiation Absorbance Device(s) (RAD) then take a measurement of the various radiations emitted by the sample over a pre-determined period of time. To determine the presence and quantity of pre-selected individual fluids, the analyser system having magnified the data of the scan, matches and analyses the wavelengths specifically concerned and their peak intensities against known data already stored in the fluid data base. Alternatively, the preferred method of detecting fluids that are unknown at the time of sampling is to utilise the full range of the Radiation Absorbance Device(s) (RAD), whether sub-infra sonics, infra sonics, sonics, ultra sonics, microwaves, infra red, ultra violet, x-ray, gamma, cosmic and ultra-cosmic. In the preferred operation the process variables such as temperature, pressure and humidity are then measured and recorded again. The fluid analyser system software can then not only determine the fluids present in the sample through a databank of the known wavelengths of fluids, but can also compute the amounts of each identified fluid present through the measurement of the fluid intensities.

The data that is collected by the analyser is preferably calibrated which may include amongst other computations and subtraction of a dark level reading. A dark level reading, records measurements of what is present in the closed consistent light environment chamber without the receptacle inside, under the same pre-determined time duration as the fluid sample analysis without the excitation device in operation. Using the Radiation Absorbance Device(s) (RAD) receive and absorb, radiation from the radiation source and record the values measured. The radiation source is the atmosphere and its surroundings within the consistent light condition environment. A dark level reading may also provide for the inclusion of an inflated receptacle within the consistent light environment. We have found that the dark level reading may be taken at the time of sampling, prior to sampling or can be pre-recorded. We prefer to take the reading on the day, at the location of the sample being analysed allowing for the current dark level variables to be taken into account. Repeating the process any number of times will provide an increased accuracy through averaging.

This calibrated data is preferably magnified using standard curve fitting and signal magnification techniques which can incorporate multiplication and spectral splitting of the pixels. The magnified signal may then be used to identify the fluids present in the sample via the software. This is achieved by comparison against a stored information bank of known wavelengths of fluids. Each molecule of a differing nature will have differing levels of resonance or wavelengths. The system preferably uses software that can calculate the absorbances at each of the particular values during or after the radiation measurement, to give the quantity present of each of the fluids which have been identified, within the spectral range (nm) of the Charge-Coupled Device (CCD) detectors being used within the RADs. Knowing the volume of the inflated receptacle used, the fluids are expressed as a percentage of the sample(s). The accuracy of the measurement may be increased by taking multiple measurements of one or more samples.

All fluids at the time of sampling will be analysed under the same conditions using the same degree of sample activation. Even though each sample's process variables such as temperature or pressure may differ. The intensity values recorded will be in proportion at the time. The individual values of intensity are not as important as the relationship they have as a portion of the whole. Therefore, if temperature changed, the registered intensity values throughout the spectra analysed will change accordingly at the time. Consequently, the volumes identified will be in accordance to the process variables at the time and location of sampling. The temperature variance is important as changes to the registered and non-registered intensity values are not linear when expansion and retraction occur.

Having been able to identify the fluids present with their volumes expressed as a percentage of the sample, many characteristics of the fluids, such as weights and sizes can be determined. This will help construct a far more comprehensive picture and moving model of fluids and their real time activities.

The invention is illustrated by the accompanying FIG. 1 which is a cross section of the sample analysis section of an apparatus such as that described in PCT Application WO 03/044503.

In the FIG. 1, is the light consistent environment chamber, and 2 is the container containing the sample to be analysed. 3 is a radio frequency discharge device, and 4 is a pin or remainder of discharge circuit to attract the discharge through the sample contained within container 2. 5 is a radiation absorption device for measurement of the radiation emitted by the activated sample. Accordingly when the radio frequency device 3 is activated the discharge ('lightening') passes through the FEP walls of the container 2 and excites the molecules contained within the container. This activation continues for the duration of the scan. The raw data is then subjected to various CCD calibration equations and subtractions of noise (dark level readings and signatures etc) having been through a process of magnification and averaging. The results are generated in less than 1 minute. The analysis system is then immediately ready for the next sample run avoiding any sample or probe contamination.

FIGS. 2 to 9 show the preferred receptacle which may be use in the present invention and is also an embodiment of the present invention.

Figure 2:
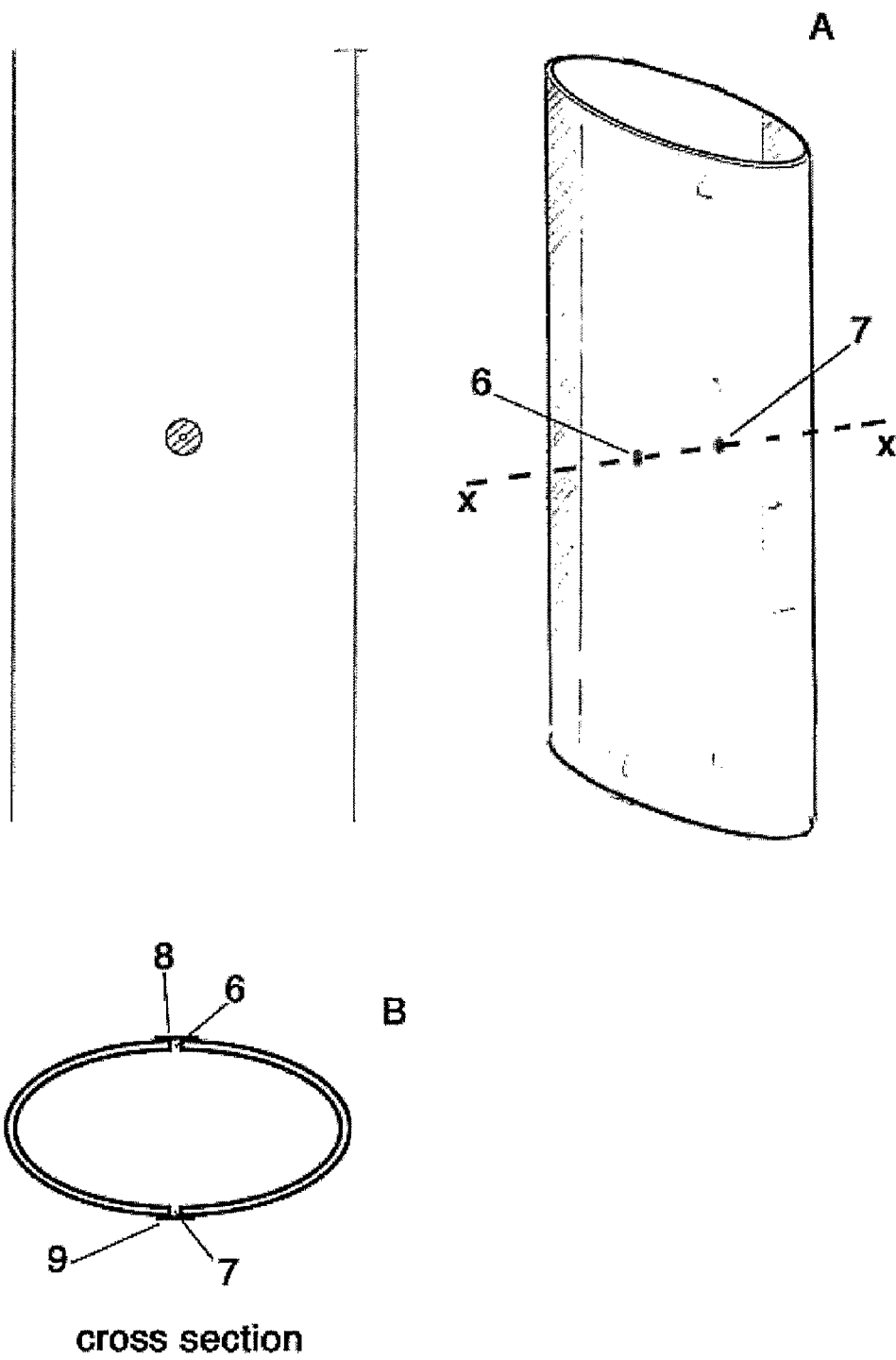
Figure 3:
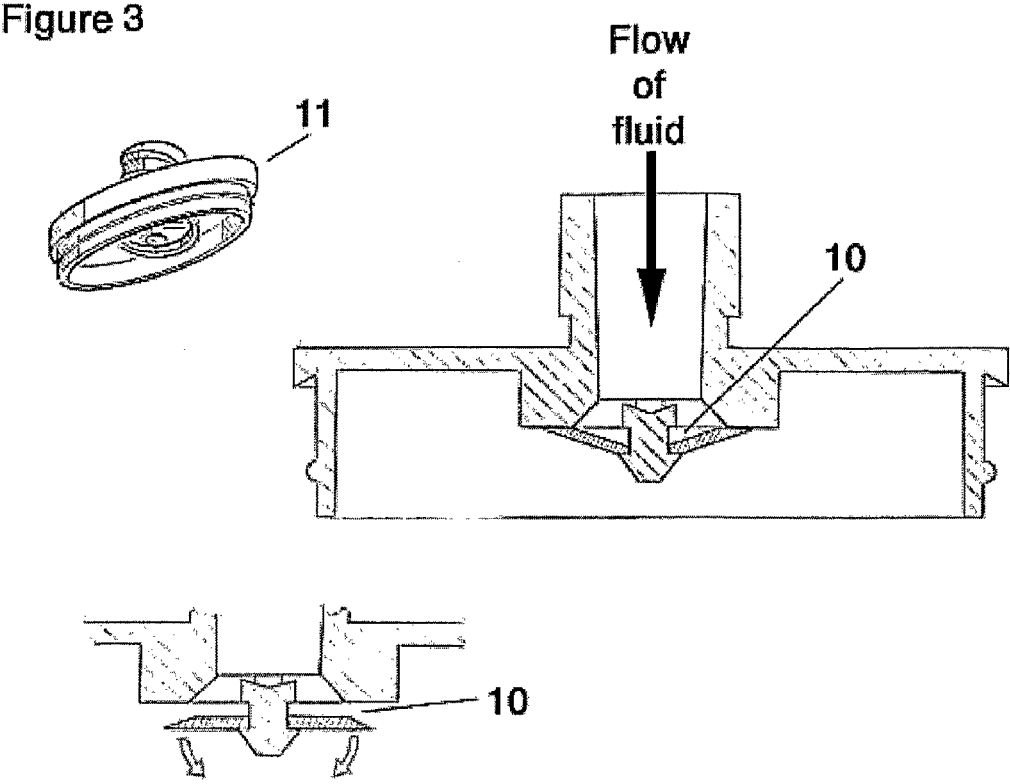
FIG. 3 is a view of the top of a receptacle comprising a non-return valve and a non-return valve holder.
Figure 4:
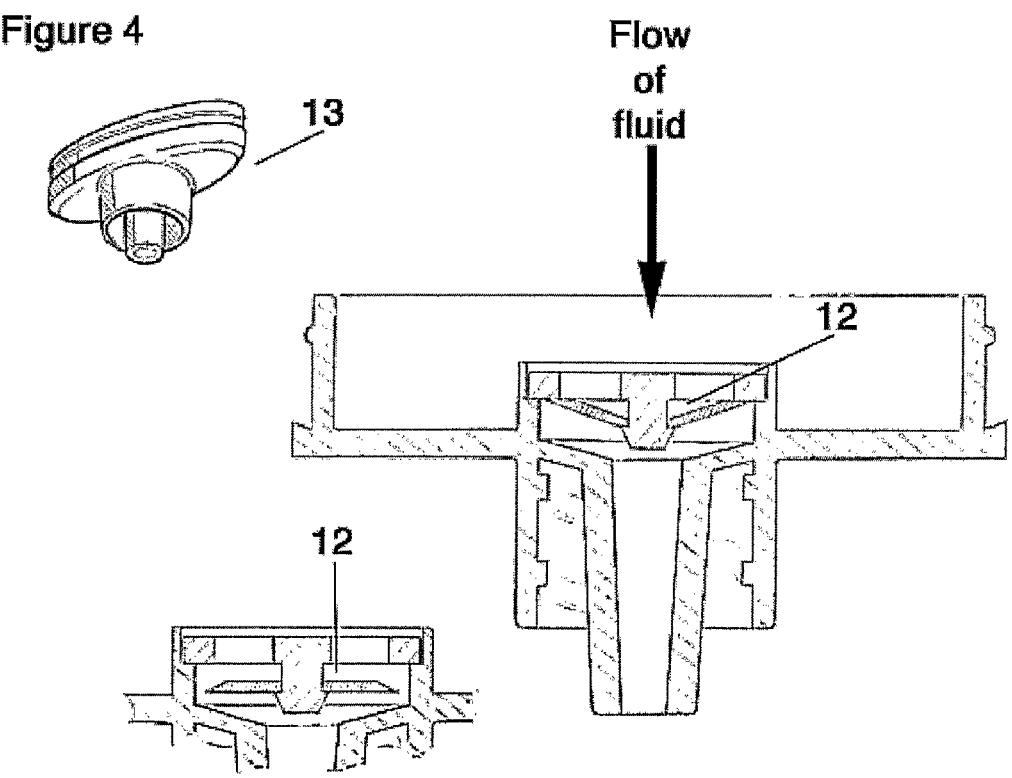
FIG. 4 is a view of the bottom of a receptacle comprising a non-return valve and a non-return valve holder.
Figure 8:
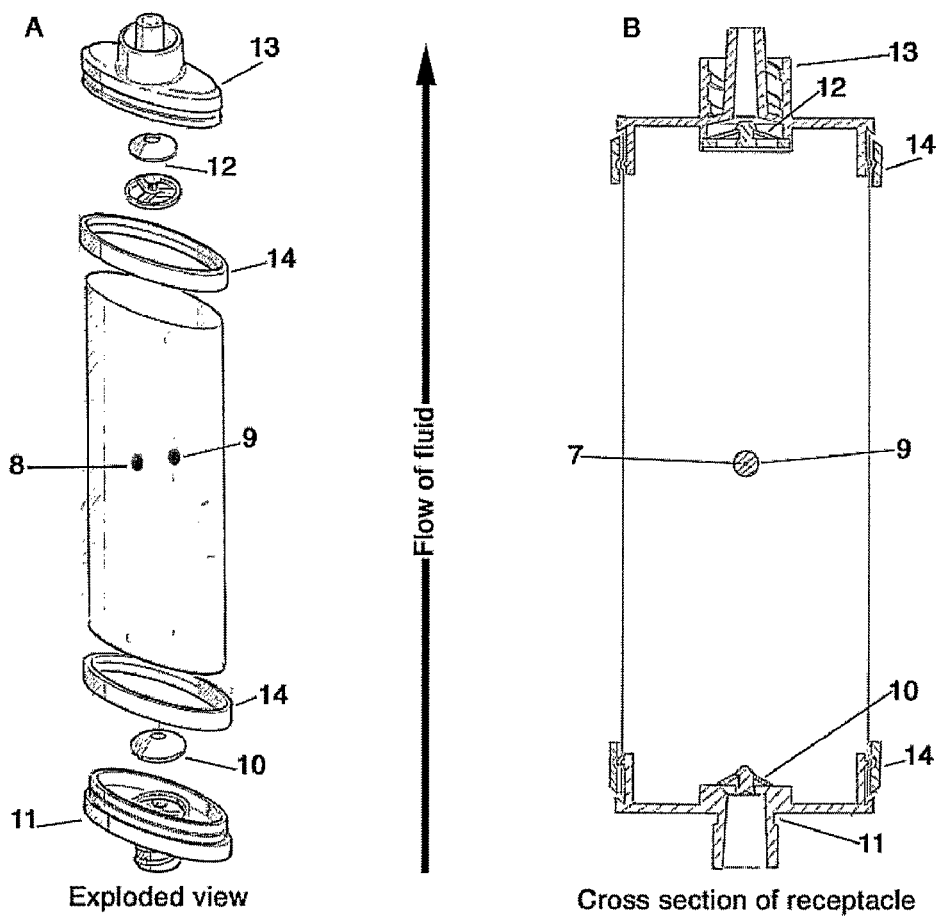
FIGS. 8a and b are an exploded view and cross-sectional view of a receptacle according to an embodiment of the present disclosure having a fluid delivery tube such as a mouthpiece.
Figure 9:
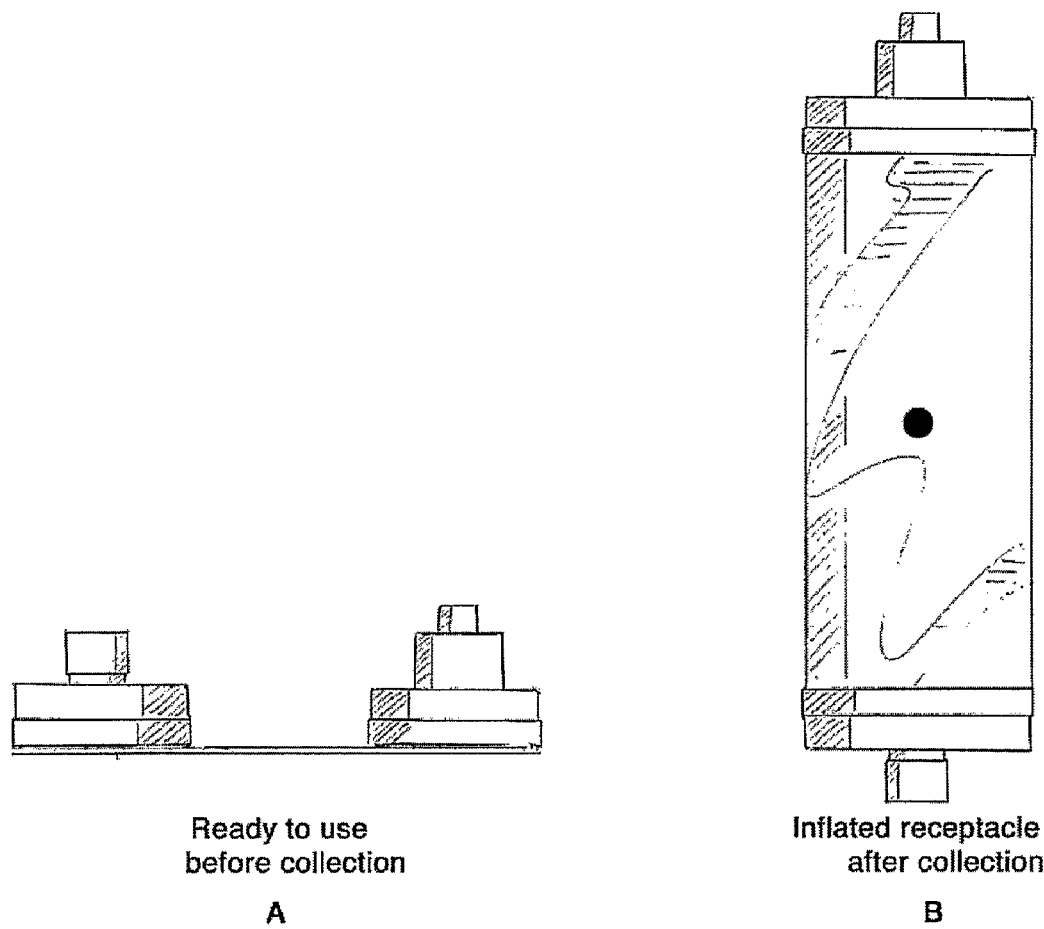
FIG. 9a shows how the sample bags appear in a collapsed state.
FIG. 9b shows a bag in its inflated form.

The preferred receptacle is made from a combination of the following seven pieces,
1) the sample bag itself, FIG. 2
2) the top comprising a non-return valve and non-return valve holder, FIG. 3
3) the bottom comprising a non-return valve and non-return valve holder FIG. 4 or
4) the bottom comprising a solid or flexible but not elastic base with no valve FIG. 5
5) the bottom comprising the sample bag sealed to itself, FIG. 6
6) tamperproof clips and/or a weld to seal the sample bag to the valve holder(s) FIG. 7
7) a fluid delivery tube such as a mouthpiece, FIG. 8.

Typically the receptacle itself is made from five pieces, the sample bag itself, the top comprising a non-return valve and non-return valve holder, the bottom comprising a non-return valve and non-return valve holder, tamperproof clips to seal the sample bag to the valve holders and a fluid delivery tube such as a mouthpiece as shown in FIG. 8. Other differing arrangements using combinations of the pieces of the preferred receptacles (FIGS. 1 to 7) to form a receptacle are also illustrated in PCT Publication WO 03/044503.

FIG. 2A shows the sample bag provided with two pinholes (6) and (7) in its side walls and illustrates how these pinholes match up with the device (3) which provides the activation discharge. In this way the discharge path is controlled to be between 3 and 4 as shown by the dotted line in FIG. 1.

FIG. 2B shows a cross section through the line X-X of FIG. 2A showing the pinholes 6 and 7 sealed with pieces of aluminium tape (8) and (9).

FIG. 3 shows a non-return valve (10) which may be provided at the top of the receptacle together with a valve holder (11).

FIG. 4 shows a similar non-return (12) which may be provided at the bottom of the receptacle together with valve holder (13).

FIG. 8A is an exploded view of the entire receptacle showing how it may be assembled with the tamperproof rings (14) (Shown in FIG. 7) and FIG. 8B is a vertical cross section of the receptacle of FIG. 8A in its assembled form.

FIG. 9A shows how the sample bags can be provided in a neat collapsed state and FIG. 9B shows a bag in its inflated form. The user can control the flow of fluid through the receptacle to collect a snapshot of the desired sample.

It is possible to weld the sample bag to itself or to the valve holders providing the valve holders are made of materials of a similar nature to FEP or of FEP itself, but, for economic reasons we prefer the valve holders to be made from materials such as medical grade polypropylene. In this instance we prefer to provide a tamperproof clip seal. The valves may be injection moulded from materials such as silicon. The valve holders and valve holder tamperproof clips may also be injection moulded as can the fluid delivery tube also from materials such as medical grade polypropylene. In which ever arrangement, a vacuum is created within the receptacle, then sterilised and (vacuum) packed to avoid contamination prior to use. The valve holder is preferably shaped so that a fluid delivery tube, such as a mouthpiece can be readily attached to the top of the receptacle. In use the vacuum packed seal(s) of the receptacle is broken, the sample collected through the conduit/delivery tube from the pressure of the flow of for example exhalation and/or emission. Alternatively the receptacle may be filled through a conduit/syringe so that a sample from the environment is collected. This can be achieved by either attaching a syringe to the bottom valve holder of the receptacle and drawing the fluid to be collected through the receptacle or by attaching a syringe to the top of the receptacle valve holder and injecting the fluid into the receptacle. Alternatively the sample bag is packed in a concertina style like an accordion or bellows and the fluid can be drawn into the receptacle inflating the sample bag. The valve(s) automatically returns to its closed position either once the motion of the flow has stopped, the pressure from the flow is less than the force of the valve to return to its closed position or the receptacle has inflated to its full capacity due to its inelastic nature.

In the preferred embodiment of the invention the receptacle provides a non-pressurised sample collection method due to the fact there is no additional power or assistance required other than that of the flow of the fluid being collected and/or pulling/injecting motion. This helps to maintain the integrity of the sample. The receptacle once full is sealed by the valve(s) and therefore the sample cannot be contaminated and furthermore is isolated from the fluid analyser system. The receptacle is preferably used only once to maintain the integrity of the collected sample, it can then be disposed of carefully or the individual components making the receptacle can be dismantled for recycling.

Two or more receptacles may be linked in series to allow parallel analysis of more than one sample. Caps may also be fitted to the valve holder(s) to ensure there is no escape of or contamination to the collected sample whilst in transit for example.

The shape of the inflated receptacle should be such that it is a firm fit within the consistent light condition environment of the fluid analyser. We prefer that the receptacle, upon inflation by the fluid to be analysed is oval at the point where the radiation detectors are positioned. The valve and the materials from which the container is made should be such that the container cannot be expanded beyond its original capacity due to inflation by the pressure of the sample.

An analysis, typically takes between 25 and 40 seconds and is performed by collecting a sample of the fluid to be analysed in the container and placing the container in the constant environment chamber. The test is then started and the temperature and optimally the humidity/dew point and atmospheric pressure of the chamber 3 are determined. The radio frequency activation device 3 is then activated as are the radiation detector(s) 3 and a measurement of the radiations emitted by the fluid sample is taken over a pre-determined duration and recorded. According to the nature of the test several samples may be analysed or the sample may be subjected to several measurements. The data storage allows for the capture of a wide range of additional data appropriate to the nature of the sample. For example if the analysis is of breath, perhaps for medical purposes, then the location (at work, at home, travelling etc) can be recorded as can (indoors, outdoors, underground). Similarly the climatic conditions can be recorded as can the exact date, time and location at which the sample was taken.

Figure 10:
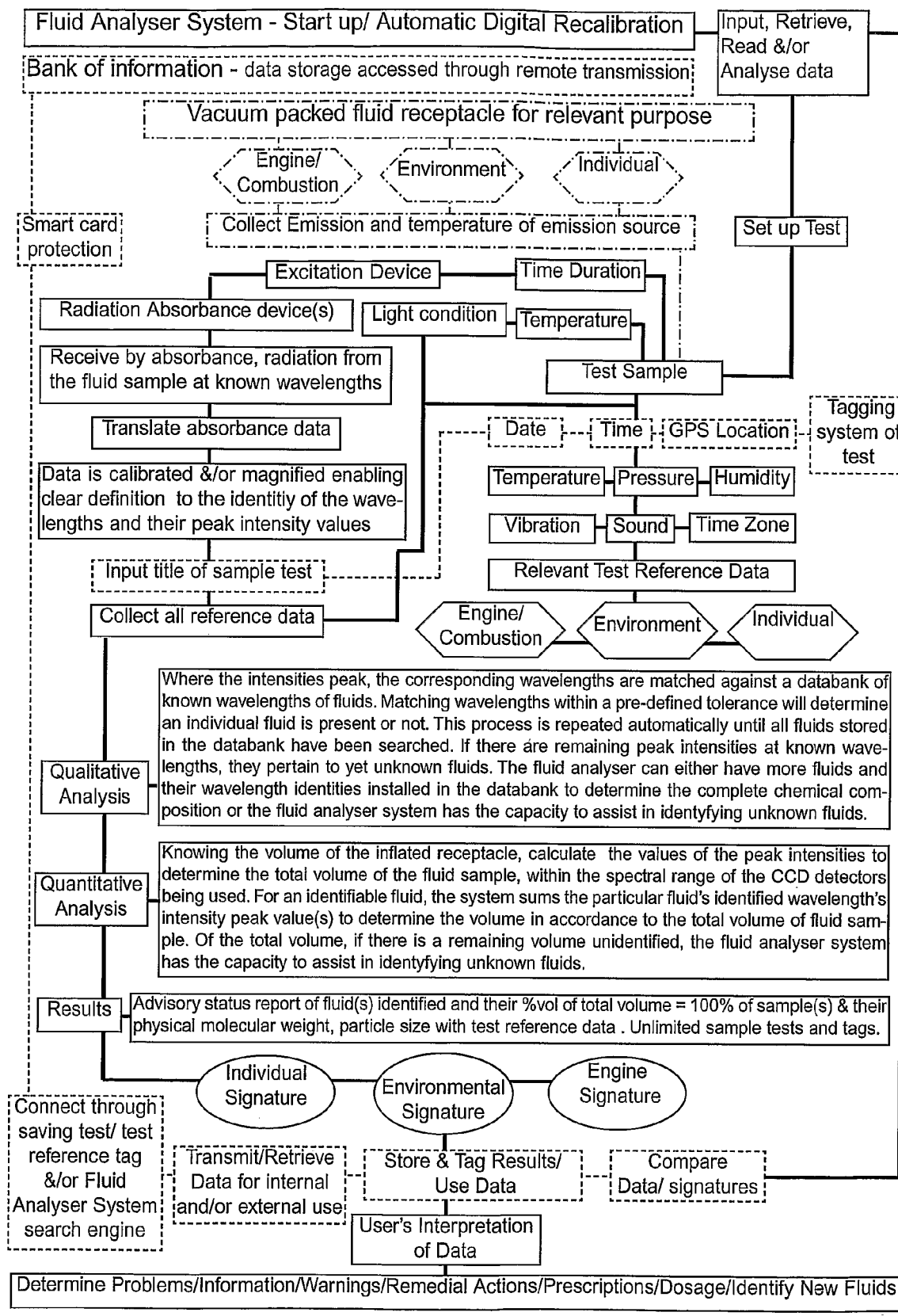
FIG. 10 is a schematic flow diagram of the performance of the system of the present disclosure.

FIG. 10 is a schematic flow diagram of the performance of the system of the present invention. The user/controller has the ability to install data into the fluid analyser system's database by means of downloading information, installing from a disc, and/or a user/controller inputting data. In addition each test result can be stored and may be automatically tagged by the user's title of the test, date, time and GPS location. The test is preferably, but not necessarily, stored chronologically and externally either in a bank of information.

The information obtained can then be stored and tagged for subsequent use for instance in forensic operations. The results can also be compared with existing data. Alternatively the data can be interpreted to provide warnings of the presence of dangerous fluids, environmental changes leading to storms and earthquakes and other natural phenomena. Alternatively the data can be interpreted for medical purposes for the diagnosis of illnesses and the prescription of medicines as an advisory system. The information can also be used to give a particular signature to the source of the sample for example; the accuracy of the techniques of the present invention enables unique individual breath signatures to be obtained somewhat like an individuals DNA profile. Having a unique individual signature registered could be most useful in other areas such as security, insurance and personal identity ratification. Replicating the individual signature, that is specific fluids in their concentrations, will not be possible. The fluid analyser system may be used for the purpose of predictions. For example, indications from a trend or signature that a person may have an illness developing which could be prevented if identified at an early stage.

Data analysis may be performed using the various techniques described in PCT published application WO 03/044503.

The Examples of additional data that may be stored include one or more of external data such as height, weight, age, body mass, body surface area, lung capacity, blood type, blood analysis including blood pressure, hydration levels, blood sugars, blood testosterone, blood oestrogen levels and cholesterol. Blood flow, chill factors, reflection, respiration rate, pulse, gender, ethnicity, posture, lifestyle, supplementary lifestyle, location, supplementary location, molecular size, molecular weight, gravity, activities and calorific values.

The fluid analyser system of the present invention can be used for clinical studies. In a study of Asthma, as one example of many, there would be a qualitative and/or quantitative difference not only between asthmatics and non-asthmatics but also between asthmatics of differing clinical manifestation, or variation within an individual sufferer on occasions of different physiological status. In this way the fluid analyser system will not only have the ability to screen for the presence of certain fluids associated with diseases or illnesses, but be able to monitor severity and long term fluctuation. In addition to the clear clinical diagnostic potential, the fluid analyser system will also be able to analyse components in the environment which may trigger or increase the risk of certain conditions, such as sensitising agents and allergens important to atopic eczema, and other respiratory illnesses.

The results generated from the fluid analyser system can be used as markers. These markers will be known as signatures and can be used as overlays for comparative analysis by the users for status reports, acting as an advisory system only. Using the advisory data together with other outside information and technologies, the users have the potential to determine problems, diseases and illnesses, diagnosis, individual dosage, standards and prediction, designer medication, warnings and alarms, remedial actions and new fluids.

Another benefit of the fluid analyser system is that it is able to provide the user with instant data. The resulting advisory status report can be understood and appreciated by a wider user group immediately preventing event driven courses of action and decision making creating a more proactive approach.

Examples of the information that may be pre-recorded and put into the fluid analyser system's database for comparative analysis are as follows:

1. Known data taken as a standard of environmental and the individual norm for fluids. From 0- to 100% of normal volume with proposed splits of measurements to form a template. For example, Nitrogen is from 0- to 100% of normal volume with increments of at least 0.0000000001%.
2. Known physical environmental data extended up and down the normally accepted scales of measurement with further extensions both up and down the scale as found in artificial environments. From 0- to 100% of normal volume with proposed splits of measurements to form a template. For example, temperature is −100° C. to +100° C. with increments of 0.00001° C.
3. Known physical data tables of individuals recording all parameters also relating to breath gases extended up and down the normally accepted scales of measurement with further extensions both up and down the scale. From 0- to 100% of volume with proposed splits of measurements to form a template.
4. Recorded as actual measurements of the environment on the day (including temperature, pressure, humidity) and at the time of the collection of the sample. With the facility to overlay against the pre-recorded known data listed above under 1 to 3, this may include dark level reading.
5. Recorded as actual individual physical tests on the day and at the time of the environmental test. With the facility to overlay against the pre-recorded known physical data listed under 1 to 4.
6. Databank of known wavelengths of fluids. Any methodology may be used to add a new fluid to the database. However, we prefer to set the temperature of the fluid system analyser, under normal ambient conditions, record measurements of what is present in the consistent light environment chamber without the receptacle inside, for a pre-determined time without the excitation device in operation (dark level reading). Using the Radiation Absorbance Device(s) (RAD) receive and absorb, radiation from the radiation source and record the values measured. The radiation source is the atmosphere and its surroundings within the consistent light condition environment. Next the receptacle is filled with the pure fluid, Nitrogen gas for example, and placed into the consistent light condition environment and the temperature set. Under a pre-determined time duration including the use of the discharge device activating the molecular content of the receptacle, the fluid analyser system's Radiation Absorbance Device(s) (RAD) receive by absorbance, radiation from the, Nitrogen, which is known wavelengths. The recorded data initially goes through a process of calibration calculations and then through standard techniques through standard techniques the values are magnified enabling a clearer definition as to the identity of the wavelengths and their peak intensity values. Repeating the process any number of times will provide an increased accuracy through averaging. What is considered to be distortion and noise via a process of elimination referencing other known data, such as the excitation device which has a known signature, other samples taken, the impact of the receptacle itself, the light environment compartment and the actual dark level reading all of which can be subtracted from the retrieval sample reading. The remaining peak intensity wavelength values provide an identity. In this example, Nitrogen.
7. Actual wavelengths act as indicators to mark their peak intensity measurements. Where the intensities peak, the corresponding wavelengths are matched against the databank, established as set out in 6 above, of known wavelengths of fluids. Matching wavelengths within a pre-defined tolerance will determine the presence of an individual fluid. This process is repeated automatically until all fluids stored in the databank have been searched and the fluids in the sample identified. Points 4, 5 and 8 relate to and/or incorporate 7 via their definitions.
8. Actual absorbance data of intensities to determine volumes of identified fluids. When used for health purposes this can illustrate excesses and depletions of the norm and/or trends.

The content of the sample having been determined the software can be programmed to enable the following comparisons to be made:

A. The data recorded under 4 above is compared with the data under number 1. With a list of numerical comparatives and +/−% variances shown. With numerous tests per individual, a trend or more accurate mean and degree of +/−% variance of the extrapolated data can be established against the norm listed in the pre-recorded data of 1 above.
B. The data recorded under number 5 above is compared with the data under number 1. With a list of numerical comparatives and +/−% variances shown. With numerous tests per individual, a trend or more accurate mean and degree of +/−% variance of the extrapolated data can be established against the norm listed in the pre-recorded data of 1.

C. The data recorded under number 5 above is compared with the data under number 3. With a list of numerical comparatives and +/−% variances shown. With numerous tests per individual, a trend or more accurate mean and degree of +/−% variance of the extrapolated data can be established against the norm listed in the pre-recorded data of 3.

D. The data recorded under numbers 4 & 5 above is collectively to be compared with the data under numbers 3 & 2. Together with a list of numerical comparatives and +/−% variances shown. With numerous tests representing the samples, a trend or more accurate mean and degree of +/−% variance of the extrapolated data can be established against the norm listed in the pre-recorded data of 3 & 2.

E. The data recorded under number 4 above is compared with the data under number 2. Only with a list of numerical comparatives and +/−% variances shown. With numerous tests representing the sample, a trend or more accurate mean and degree of +/−% variance of the extrapolated data can be established against the norm listed in the pre-recorded data of 2.

F. The data recorded under numbers 1 & 4 is compared with the data under numbers 1 & 5. Only with a list of numerical comparatives and +/−% variances shown. With numerous tests representing the sample, a trend or more accurate mean and degree of +/−% variance of the extrapolated data can be established against the norm listed in the pre-recorded data of 2.

G. The data recorded under any of numbers 1, 2, 3, 4 or 5 may be compared with previous internal and/or external sample readings and/or data.

H. Historical number 1, 2, 3, 4 or 5 readings may be compared with previous internal and/or external sample readings and/or data.

I. The data recorded under number 5 may be compared with number 4, compared with previous internal and/or external sample readings and/or data.

J. Historical Number 5 may be compared with historical number 4, and may be compared with previous internal and/or external sample readings and/or data.

K. Including 7 and 8 comparisons made from A, B, C, D, E, F, G, H, I and J or combinations of.

These comparisons are particularly useful if the fluid analyser is to be used for medical purposes monitoring human breath, for example, by comparing the actual results of the analysis of the individual's breath and the environment to the normal signature taken from their breath analysis and what is normally expected to be found in that environment, the fluid analyser system will provide data assisting in an independent diagnosis as to whether an individual's problem was triggered by the environment or not. This is achieved by carrying out comparative studies using the fluid analyser system software.

By using the fluid analyser system the user has the potential to determine through comparative analysis, for example, whether or not an athlete has been involved with performance enhancing drugs.

One of the primary uses is as a means of analysing collected fluid samples to detect and quantify specific compounds, or combination of compounds. The results generated can become markers. These markers will be known as signatures and can be used as overlays for comparative analysis by the users for status reports, acting as an advisory system only. Using the advisory data together with other outside information and technologies, the users can determine problems, diseases and illnesses, diagnosis, individual dosage, designer medication, warnings and alarms, standards and predictions, remedial actions and identify new fluids. The Fluid analyser system data can be made available to the end user within 1 minute.

Figure 11:
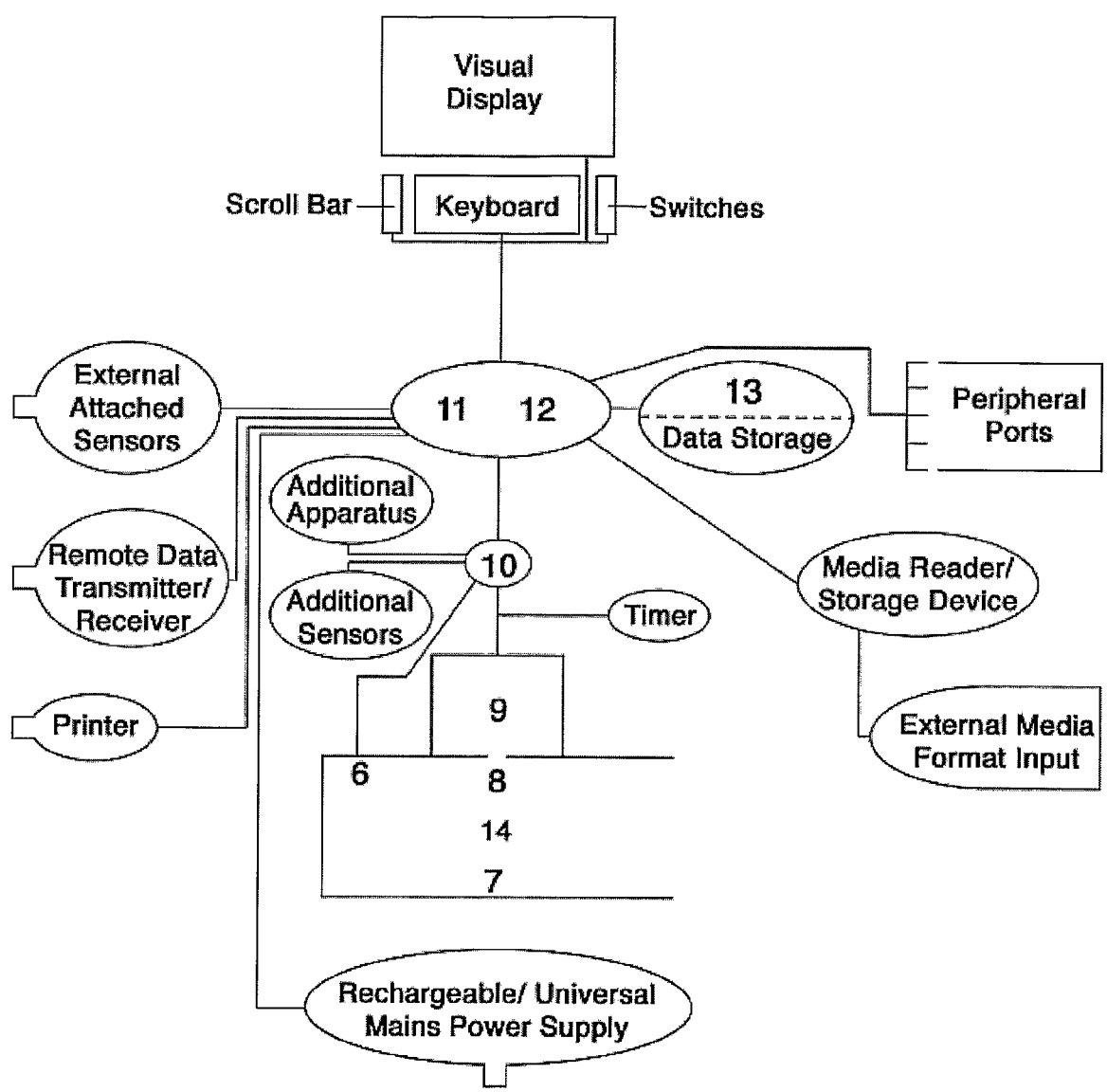
FIG. 11 is a diagrammatic illustration of the apparatus of the present disclosure.

FIG. 11 is a diagrammatic illustration of the apparatus of the present invention. The apparatus consists of a consistent light environment chamber (6) into which the inflated receptacle of FIGS. 2 to 9 can be fully inserted. The apparatus is provided with a lid (not shown) so that when closed the consistent light environment chamber and the inflated receptacle remain in a controlled light environment. The apparatus is provided with sensors which determine the temperature in the consistent light environment chamber, the temperature of the fluid sample and the level of light.

The analysis process can be activated through the interface controller such as described in Application WO 03/044503 which simultaneously activates a timer. Once the radiation absorption device(s) (9) and the excitation device (14) are activated, they start recording the radiation from the sample and the timer records the duration of the measurement which stops once the pre-determined duration time has elapsed. The measurement concerning the intensity levels detected by the RAD(s) at known wavelengths is transferred to a computer system (11) and (12) where the signal is translated and magnified. The peak intensity wavelengths are then identified and transmitted to be referenced against a database (13) of known data of wavelengths of fluids to determine the identity of fluids present. The computer (11) also provides means for calculating the total and individual volumes of fluids present referenced against the known volume of the receptacle and the process variables. To determine dark level readings through interface controller (10) the excitation device (14) may not be activated and the receptacle may or may not be in the consistent light environment chamber (6).

Preferably, the present invention also contains the features or combinations thereof shown in FIG. 11.

In addition to the fluid analyser system having the ability to be linked to multiple fluid analyser systems or peripheral devices for the purpose of transferring, comparing, referencing and/or using data multiple fluid analyser systems may be present in one form. For example, there may be any number of light consistent environment chambers (6), sensors (7), RADs (9) and excitation devices (14), configured arrangement of FIG. 11 and linked into the computer system (10), (11), (12) and (13), to analyse collected samples. The collected samples' measurements can be recorded singly, simultaneously or in combinations thereof through controller (10). Additionally, different types of fluid receptacles may be used at anyone time or combinations thereof to determine a variety of environmental conditions within a particular site. The respective light consistent environment chambers are able to receive the differently shaped fluid receptacles accordingly. This flexibility allows for multitasking to be completed utilising just one Fluid analyser system with all work being carried out at the same time.

Furthermore, for identification purposes only, it is possible by different arrangement of the fluid analyser system to identify the content of individual fluids in the outer environment where the fluid analyser is located. For instance the RAD(s) may be positioned in such a way that the radiation source is the atmosphere or other fluid sample of the environment. This fluid analyser system may be used for the purpose of determining whether a particular dangerous or potentially hazardous gas or gases are present in the atmosphere in which people need to operate, for example.

Staged timing throughout a 24 hour day using multiple sample containers inserted within the controlled environment chambers for automatic monitoring of the climatic register of the atmosphere will record regular comparative data altered by time and the process variables within the current environment.

All data received from the fluid analyser system sensors is either magnified and/or averaged via multiple sampling to a greater degree of accuracy.

FIG. 12 is a flow chart of an information flow during an analysis performed according to the present invention.

The invention claimed is:

1. A fluid analyser system comprising; a receptacle(s) for the collection of a fluid sample and; an analysis apparatus containing a consistent light condition compartment into which the receptacle containing the fluid sample may be placed; means external to said receptacle(s) to provide an excitation discharge within the consistent light condition compartment for activating the molecules within the sample; means for detecting the radiation emitted by the sample and for generating a signal indicative of said radiation emitted; and means for magnifying the signal wherein the receptacle is provided with pinholes covered by metallic contacts to be positioned against the means to provide the discharge to control the discharge through the sample when the receptacle is positioned within the consistent light condition compartment for analysis.

2. A fluid analyser system according to claim 1 comprising means for translating the magnified signal into the nature and quantity of the fluids present in the sample said means being referenced according to:
  a) the known volume of the inflated receptacle
  b) the light condition of the fluid sample
  c) the temperature of the fluid sample
  d) the duration of a radiation scan and/or
  e) the distance of the radiation scan.

3. A fluid analyser system according to claim 1 in which the analyser system is non-invasive.

4. A fluid analyser system according to claim 1, wherein said system is capable of transmitting and/or receiving test data remotely.

5. A fluid analyser system according to claim 1 including one or more of a visual display screen, a printer, a data transmitter/receiver, data storage, rechargeable/universal mains power supply, peripheral ports, keyboard, scroll bar, switches.

6. A fluid analyser system according to claim 1 a comprising a database of fluids and their known wavelengths.

7. A fluid analyser system according to claim 1 which is portable.

8. A fluid analyser system according to claim 1 in which walls of the receptacle have a high optical clarity and are flexible but not elastic.

9. A fluid analyser according to claim 1 in which the receptacle is formed from a fluorocarbon polymer.

10. A fluid analyser according to claim 1 in which the receptacle is formed from a medical grade polypropylene.

11. A fluid analyser according to claim 1 in which the receptacle is provided with a one-way valve.

12. An analyser according to claim 11 in which the valve is in a valve holder which is shaped so that a fluid delivery tube, can be attached to the top of the receptacle.

13. A fluid analyser according to claim 11 in which the valve is in a valve holder which is shaped so that another receptacle or attachment can be attached to the bottom of the receptacle.

14. A fluid analyser according to claim 1 in which the shape of the inflated receptacle is such that it is a firm fit within the consistent light condition environment.

15. A fluid analyser according to claim 1 containing means whereby the peak intensities and peak intensity values are used/calculated and/or correlated with known/unknown peak intensities and/or peak intensity values (nm wavelength values) to indicate the nature of the fluids present in the sample and to determine the concentrations of the fluids in the sample.

16. A fluid analyser system according to claim 1, further comprising means for enhancing the signal from the radiation emitted by the sample.

17. A fluid analyser system according to claim 1, further comprising a timer to measure the duration of the time the means for the detecting the radiation is exposed to the radiation emitted by the activated fluid sample, during or after the excitation discharge.

18. A fluid analyser system according to claim 1, wherein the excitation discharge is a radio frequency discharge such as a radio frequency discharge Telsa Coil or other electric discharge.

19. A fluid analyser system according to claim 1, further comprising means for translating the signal into the nature and concentration of the fluids present in the sample said means being referenced according to:
  a) the light condition of the fluid sample and
  b) the duration of the radiation scan.

20. A fluid analyser according to claim 1, wherein said metallic contacts are of aluminium adhesive tape.

21. A fluid analyser according to claim 1, wherein the excitation discharge is transverse to the absorption device.

22. A fluid analyser system according to claim 1, further comprising a light meter for determining the consistent light condition environment.

23. A fluid analyser according to claim 1, further comprising computer driven software to provide an advisory status report on the content of the fluid and the conditions under which the analysis was performed.

24. A fluid analyser according to claim 1, wherein the sample may be taken at one location, scanning and analysis system may be used in the same or another location and the detection signal, is transferred to another location for analysis and/or storage or kept in the same location for analysis and/or storage.

* * * * *